United States Patent
Lee et al.

(10) Patent No.: US 10,892,736 B2
(45) Date of Patent: Jan. 12, 2021

(54) FINE DUST CONCENTRATION SENSOR

(71) Applicant: Samsung Electro-Mechanics Co., Ltd., Suwon-si (KR)

(72) Inventors: Tae Kyung Lee, Suwon-si (KR); Je Hong Kyoung, Suwon-si (KR); Jin Suk Son, Suwon-si (KR); Ran Hee Shin, Suwon-si (KR); Hwa Sun Lee, Suwon-si (KR)

(73) Assignee: Samsung Electro-Mechanics Co., Ltd., Suwon-si (KR)

(*) Notice: Subject to any disclaimer, the term of this patent is extended or adjusted under 35 U.S.C. 154(b) by 167 days.

(21) Appl. No.: 16/168,906

(22) Filed: Oct. 24, 2018

(65) Prior Publication Data

US 2019/0372554 A1    Dec. 5, 2019

(30) Foreign Application Priority Data

May 30, 2018    (KR) .......................... 10-2018-0061623

(51) Int. Cl.
| | | |
|---|---|---|
| *H03H 9/17* | (2006.01) | |
| *H03H 3/04* | (2006.01) | |
| *G01N 21/85* | (2006.01) | |
| *G01N 1/22* | (2006.01) | |
| *G01N 33/00* | (2006.01) | |
| *G08B 17/117* | (2006.01) | |

(Continued)

(52) U.S. Cl.
CPC .......... *H03H 9/173* (2013.01); *G01N 1/2205* (2013.01); *G01N 1/2273* (2013.01); *G01N 1/24* (2013.01); *G01N 21/85* (2013.01); *G01N 33/0011* (2013.01); *G08B 17/117* (2013.01); *H03H 3/04* (2013.01); *H03H 9/174* (2013.01); *H03H 2003/021* (2013.01)

(58) Field of Classification Search
CPC ............. G01N 1/2273; G01N 33/0011; G01N 1/2205; G08B 17/117
USPC ........................................................ 73/31.02
See application file for complete search history.

(56) References Cited

U.S. PATENT DOCUMENTS

| | | | | |
|---|---|---|---|---|
| 2002/0192600 A1* | 12/2002 | Okamura | ............. | B01J 19/0046 |
| | | | | 430/320 |
| 2006/0252044 A1* | 11/2006 | Okumura | ......... | G01N 33/54373 |
| | | | | 435/6.11 |

(Continued)

FOREIGN PATENT DOCUMENTS

| | | | | |
|---|---|---|---|---|
| KR | 10-2006-0004958 A | | 1/2006 | |
| KR | 101747742 | * | 1/2006 | ................ B01L 3/00 |

(Continued)

OTHER PUBLICATIONS

ISR Preliminary Report, ISA,—International Search Authority, PCT/JP2004/005878, WO2004097415. dated Apr. 25, 2003, 4 pages (Year: 2003).*

(Continued)

*Primary Examiner* — Clayton E. LaBalle
*Assistant Examiner* — Kevin C Butler
(74) *Attorney, Agent, or Firm* — NSIP Law

(57) ABSTRACT

A fine dust concentration sensor includes a bulk acoustic resonator and a cap including an upper portion with holes therein and a lateral portion connected to the upper portion to accommodate the bulk acoustic resonator. An upper surface of the upper portion of the cap is coated with a hydrophobic material.

18 Claims, 14 Drawing Sheets

(51) Int. Cl.
*G01N 1/24* (2006.01)
*H03H 3/02* (2006.01)

(56) References Cited

U.S. PATENT DOCUMENTS

| | | | | |
|---|---|---|---|---|
| 2008/0081398 A1* | 4/2008 | Lee | .................. | H01L 21/76898 |
| | | | | 438/109 |
| 2009/0071230 A1* | 3/2009 | Aubert | ............... | G01N 33/0063 |
| | | | | 73/31.02 |
| 2016/0299427 A1* | 10/2016 | Kim | ......................... | G03F 7/40 |
| 2019/0372554 A1* | 12/2019 | Lee | ....................... | H03H 9/174 |

FOREIGN PATENT DOCUMENTS

| | | | | |
|---|---|---|---|---|
| KR | 10-1747742 B1 | 6/2017 | | |
| KR | 20060004958 | * | 6/2017 | ............. G01N 21/94 |

OTHER PUBLICATIONS

Menglun Zhang et al. , IEEE Internal tional Frequency Control Symposium (FCS), Response Signal Enhancement of Film Bulk Acoustic Resonator Mass Sensor with Bounded Hydrophobic Teflon Film, IEEE, May 19-22, 2014, 5 pages (Year: 2014).*

Justin Phelps Black, EECS-2006-193, MEMS-Based System for Particle Exposure Assessment Using Thin-Film Bulk Acoustic Wave Resonators and IR / UV Optical Discrimination,EE University of California at Berkeley, Dec. 22, 2006, 163 pages (Year: 2006).*

Sanju Thomas et al., IEEE Particle Sensor using Solidly MountedResonators, IEEE, 2015, 10 pages (Year: 2015).*

Washim Reza Ali et al., Piezoelectric MEMS based acoustic sensors: A review, Elsevier, Feb. 2010, 31 pages (Year: 2010).*

* cited by examiner

I-I'

FINE DUST CONCENTRATION SENSOR

CROSS-REFERENCE TO RELATED APPLICATION

This application claims the benefit under 35 USC 119(a) of Korean Patent Application No. 10-2018-0061623 filed on May 30, 2018 in the Korean Intellectual Property Office, the entire disclosure of which is incorporated herein by reference for all purposes.

BACKGROUND

1. Field

The following description relates to a fine dust concentration sensor.

2. Description of Related Art

Recently, as air pollution has become a serious problem, demand for a sensor for measuring fine dust has increased and, in particular, interest in an acoustic resonant mass sensor as a device for measuring fine dust has increased.

A film bulk acoustic resonator (FBAR) has been known as a device for embodying such an acoustic resonant mass sensor. Such a FBAR may be advantageously mass-produced at low cost and microminiaturized. It is possible to embody a high quality factor (Q) value, which is a main characteristic of a filter and to also use the FBAR in a microfrequency band and, in particular, a personal communication system (PCS) and digital cordless system (DCS) band is also advantageously embodied.

In general, a FBAR has a structure including a resonator formed by sequentially stacking a first electrode, a piezoelectric layer, and a second electrode on a substrate. With regard to an operating principle of the FBAR, first, an electric field is induced in the piezoelectric layer by electrical energy applied to the first and second electrodes, a piezoelectric phenomenon occurs in the piezoelectric layer by the induced electric field and a resonator vibrates in a predetermined direction. As a result, a bulk acoustic wave is generated in the same direction as a vibration direction to cause resonance.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In a general aspect, a fine dust concentration sensor including a bulk acoustic resonator and a cap including an upper portion with holes therein and a lateral portion connected to the upper portion. The cap accommodates the bulk acoustic resonator and an upper surface of the upper portion of the cap includes a hydrophobic material.

An internal surface of each of the holes may include the hydrophobic material.

The bulk acoustic resonator may generate a resonant frequency or an antiresonant frequency that may be used to measure a concentration of fine dust introduced through the holes.

The bulk acoustic resonator may include a first electrode, a piezoelectric layer, and a second electrode, which may be sequentially stacked.

The holes may correspond to a region in which the first electrode, the piezoelectric layer, and the second electrode overlap each other in a stacking direction.

The bulk acoustic resonator may include a passivation layer disposed on the second electrode and a hydrophobic layer disposed on the passivation layer.

The upper portion of the cap may include one of silicon (Si), silicon on insulator (SOI), glass, a dielectric, a polymer film, and a metal plate.

Each of the holes may have a dimension in a range of 2 μm to 20 μm.

A dimension of each of the holes may be 1 to ⅕₀ times a thickness of the upper portion of the cap.

In another general aspect, a fine dust concentration sensor includes a bulk acoustic resonator including a first electrode, a piezoelectric layer, and a second electrode, which are sequentially stacked in a stacking direction, and a cap including an upper portion with holes and a lateral portion connected to the upper portion to accommodate the bulk acoustic resonator.

The holes correspond to a region in which the first electrode, the piezoelectric layer, and the second electrode overlap each other in the stacking direction.

An upper surface of the upper portion of the cap ma include a hydrophobic material.

An internal surface of each of the holes may include the hydrophobic material.

The bulk acoustic resonator may generate a resonant frequency or an antiresonant frequency that may be used to measure a concentration of fine dust introduced through the holes.

The upper portion of the cap may include one of silicon (Si), silicon on insulator (SOI), glass, a dielectric, a polymer film, and a metal plate.

Each of the holes may have a dimension in a range of 2 μm to 20 μm.

A dimension of each of the holes may be 1 to ⅕₀ times a thickness of the upper portion of the cap.

In another general aspect, an apparatus includes a cap defining an internal space and including holes in a surface thereof and a hydrophobic material covering at least a portion of the surface and a bulk acoustic resonator disposed in the internal space to generate a resonant frequency or an antiresonant frequency used to measure a concentration of particle material introduced into the internal space through the holes.

The bulk acoustic resonator may include a passivation layer and the hydrophobic material may be disposed on the passivation layer.

The bulk acoustic resonator may include a first electrode, a piezoelectric layer, and a second electrode stacked above an air cavity, and the hydrophobic material may be disposed on internal surfaces defining the air cavity.

Other features and aspects will be apparent from the following detailed description, the drawings, and the claims.

BRIEF DESCRIPTION OF DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
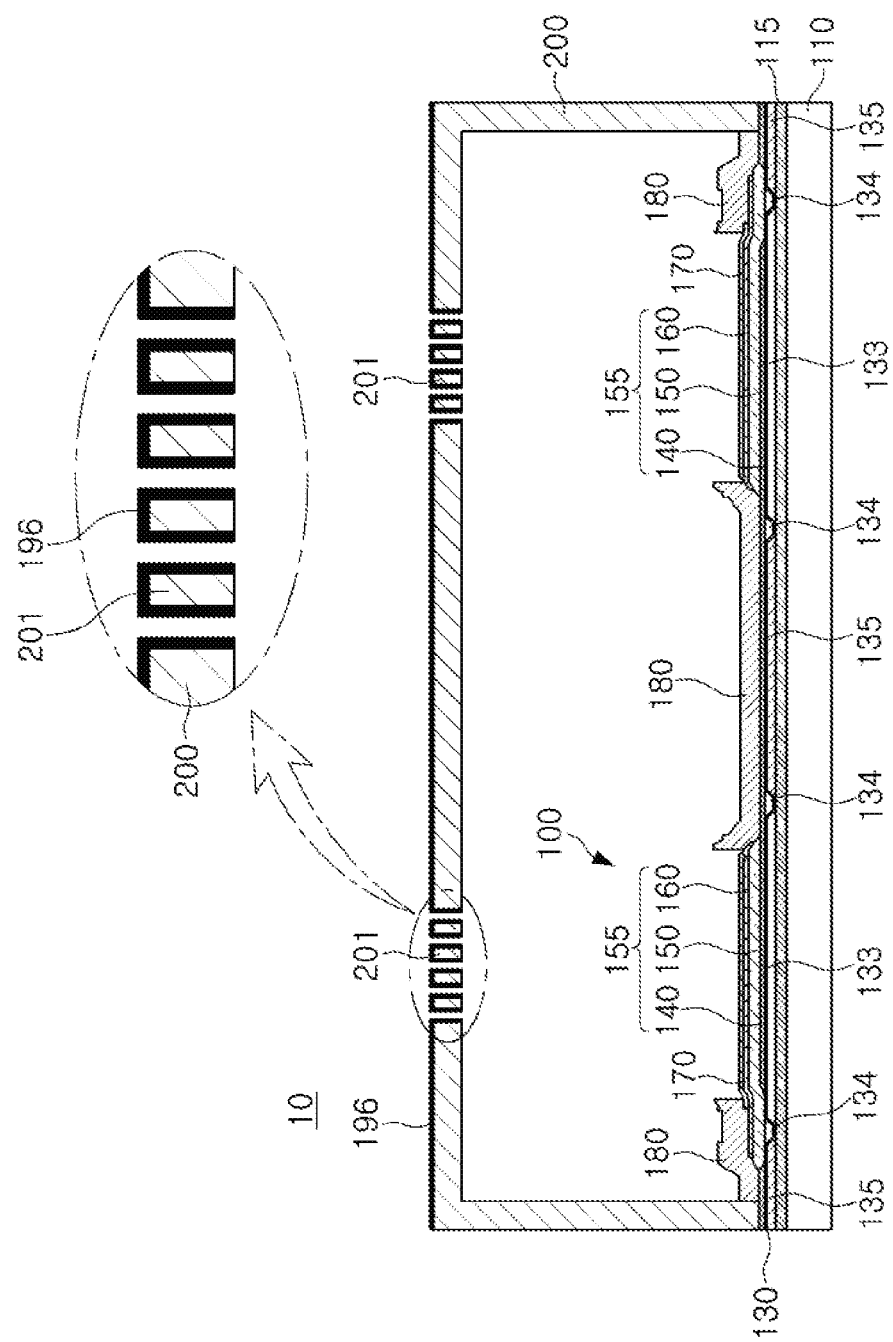
FIGS. 1 and 2 are cross-sectional views showing a fine dust concentration sensor according to an example.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Herein, it is noted that use of the term "may" with respect to an example or embodiment, e.g., as to what an example or embodiment may include or implement, means that at least one example or embodiment exists in which such a feature is included or implemented while all examples and embodiments are not limited thereto.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

As used herein, the term "and/or" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Spatially relative terms such as "above," "upper," "below," and "lower" may be used herein for ease of description to describe one element's relationship to another element as shown in the figures. Such spatially relative terms are intended to encompass different orientations of the device in use or operation in addition to the orientation depicted in the figures. For example, if the device in the figures is turned over, an element described as being "above" or "upper" relative to another element will then be "below" or "lower" relative to the other element. Thus, the term "above" encompasses both the above and below orientations depending on the spatial orientation of the device. The device may also be oriented in other ways (for example, rotated 90 degrees or at other orientations), and the spatially relative terms used herein are to be interpreted accordingly.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Due to manufacturing techniques and/or tolerances, variations of the shapes shown in the drawings may occur. Thus, the examples described herein are not limited to the specific shapes shown in the drawings, but include changes in shape that occur during manufacturing.

The features of the examples described herein may be combined in various ways as will be apparent after an understanding of the disclosure of this application. Further, although the examples described herein have a variety of configurations, other configurations are possible as will be apparent after an understanding of the disclosure of this application.

Figure 2:
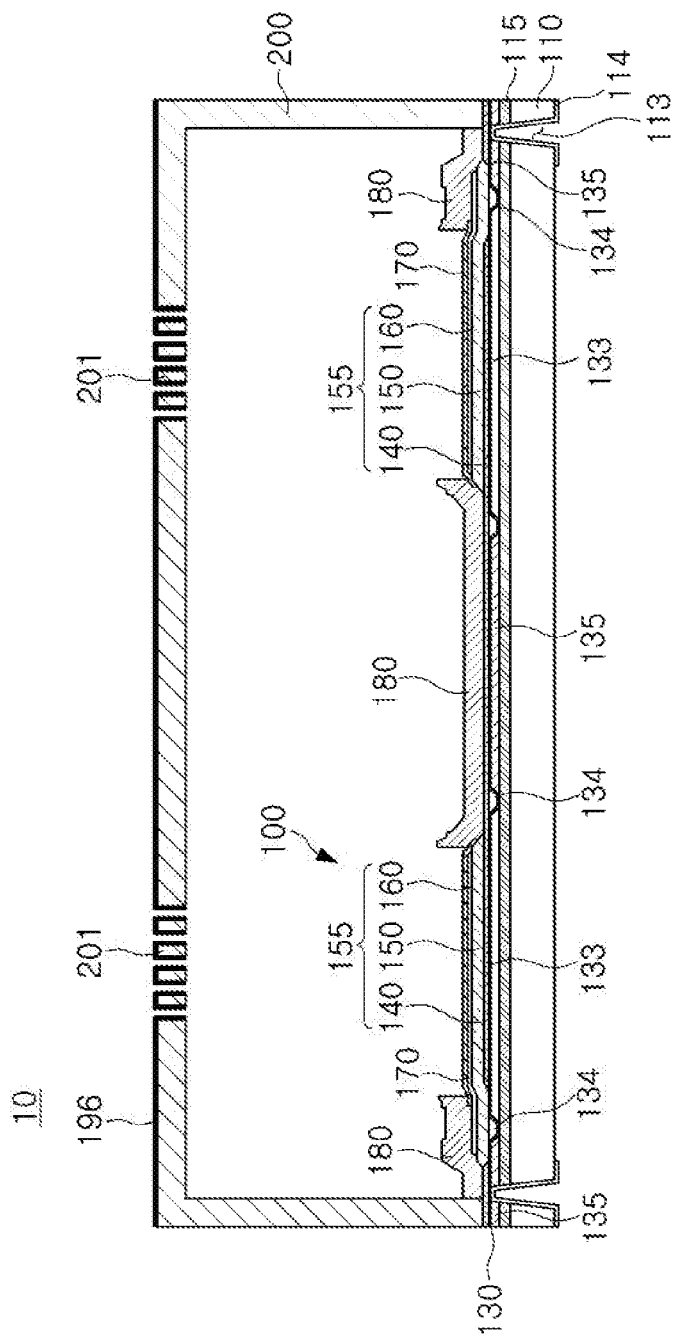

FIGS. 1 and 2 are cross-sectional views showing a fine dust concentration sensor according to an example.

The dust concentration sensors according to the example of FIGS. 1 and 2 are similar to each other and, accordingly, the dust concentration sensor according to the example shown in FIG. 1 is described and, in a description of the bulk acoustic resonator of FIG. 2, the same or repeated description of the bulk acoustic resonator according to the example shown in FIG. 1 is omitted and the bulk acoustic resonator of FIG. 2 is described in terms of a difference therefrom.

Referring to FIG. 1, a fine dust concentration sensor 10 according to an example may include at least one bulk acoustic resonator 100 and a cap 200.

Although FIG. 1 illustrates the case in which the fine dust concentration sensor 10 includes two bulk acoustic resonators 100, in some embodiments, the fine dust concentration sensor 10 may include one bulk acoustic resonator 100 or three or more bulk acoustic resonators 100. The bulk acoustic resonator 100 may be a film bulk acoustic resonator (FBAR).

The bulk acoustic resonator 100 may be configured by a stack structure including a plurality of films. The stack structure configuring the bulk acoustic resonator 100 may include a substrate 110, an insulating layer 115, an air cavity 133, a support 134, an auxiliary support 135, and a resonator 155 including a first electrode 140, a piezoelectric layer 150, and a second electrode 160 and may further include a passivation layer 170 and a metal layer 180.

A process of manufacturing the bulk acoustic resonator 100 according to an example may include the following operations. A sacrificial layer may be formed on the insulating layer 115 and a portion of the sacrificial layer may be removed to form a pattern on which the support 134 is provided. The auxiliary support 135 may be formed by the remaining portion of the sacrificial layer. A width of an upper surface of a pattern formed on the sacrificial layer may be greater than a width of a lower surface and a lateral surface of a pattern connecting the upper and lower surfaces may be inclined. The pattern is formed in the sacrificial layer and, then, a membrane 130 may be formed on the insulating layer 115 that is externally exposed by the sacrificial layer and the pattern. The membrane 130 may be formed and, then, an etch stop material, which is the base for formation of the support 134, may be formed to cover the membrane 130.

After the etch stop material is formed, one surface of the etch stop material may be planarized to externally expose the membrane 130 formed on the upper surface of the sacrificial layer. During a procedure of planarizing one surface of the etch stop material, a portion of the etch stop material may be removed and the support 134 may be formed by the portion of the etch stop material, which remains in the pattern after the portion thereof is removed. As a result of the planarization procedure of an etch stop material, one surface of the sacrificial layer and the support 134 may be approximately planarized. Here, the membrane 130 may function as a stop layer of the planarization procedure of the etch stop material.

Then, the first electrode 140, the piezoelectric layer 150, the second electrode 160, and so on may be stacked and, then, the air cavity 133 may be formed using an etching procedure of etching and removing the sacrificial layer. For example, the sacrificial layer may include poly-silicon (poly-Si). The air cavity 133 may be disposed below the resonator in such a way that the resonator 155, which includes the first electrode 140, the piezoelectric layer 150, and the second electrode 160, vibrates in a predetermined direction.

The substrate 110 may be formed of a silicon substrate and the insulating layer 115, which electrically separates the resonator 155 from the substrate 110, may be provided on the upper surface of the substrate 110. The insulating layer 115 may be formed of at least one of silicon dioxide ($SiO_2$), silicon nitride ($Si_3N_4$), aluminium oxide ($Al_2O_3$), and aluminum nitride (AlN) and may be formed on the substrate 110 via chemical vapor deposition, RF (radio frequency) magnetron sputtering, or evaporation.

The etch stop layer may be further formed on the insulating layer 115. The etch stop layer may protect the substrate 110 and the insulating layer 115 from an etching procedure and may function as a base end required to deposit a plurality of different layers on the etch stop layer.

The air cavity 133 and the support 134 may be formed on the insulating layer 115. The air cavity 133 may be formed by forming the sacrificial layer on the insulating layer 115, forming a pattern on which the support 134 is provided on the sacrificial layer, stacking the first electrode 140, the piezoelectric layer 150, the second electrode 160, and so on and then performing an etching procedure of etching and removing the sacrificial layer. For example, the sacrificial layer may include poly-silicon (poly-Si).

The air cavity 133 may be disposed below the resonator 155 in such a way that the resonator 155, which includes the first electrode 140, the piezoelectric layer 150, and the second electrode 160, vibrates in a predetermined direction. The support 134 may be provided at one side of the air cavity 133.

A thickness of the support 134 may be the same as that of the air cavity 133. An upper surface provided by the air cavity 133 and the support 134 may be approximately planarized. According to an example, the resonator 155 may be disposed on the planarized surface with a step difference being removed, thereby enhancing insertion loss and attenuation characteristics of the bulk acoustic resonator.

A section of the support 134 may be an approximately trapezoidal shape. A width of an upper surface of the support 134 may be greater than a width of a lower surface of the support 134 and a lateral surface connecting the upper and lower surfaces may be inclined. The support 134 may be formed of a material that is not etched during an etching procedure for removing the sacrificial layer. For example, the support 134 may be formed of the same material as that of the insulating layer 115 and, in detail, the support 134 may be formed of one or a combination of silicon dioxide ($SiO_2$) and silicon nitride ($Si_3N_4$).

According to an example, the lateral surface of the support 134 may be inclined to prevent an abrupt step difference from being formed at a boundary between the support 134 and the sacrificial layer, and the width of the lower surface of the support 134 may be formed to be narrow to prevent a dishing phenomenon from occurring. For example, an angle between the lower and lateral surfaces of the support 134 may be 110° to 160° and the width of the lower surface of the support 134 may be 2 μm to 30 μm.

The auxiliary support 135 may be disposed outside the support 134. The auxiliary support 135 may be formed of the same material as that of the support 134 or may be formed of a different material from that of the support 134. For example, when the auxiliary support 135 is formed of a different material from that of the support 134, the auxiliary support 135 may correspond to a portion of the sacrificial layer formed on the insulating layer 115, which remains after an etching procedure.

The resonator 155 may include the first electrode 140, the piezoelectric layer 150, and the second electrode 160. A common region at which the first electrode 140, the piezoelectric layer 150, and the second electrode 160 overlap each other in a vertical direction may be positioned above the air cavity 133. The first electrode 140 and the second electrode 160 may be formed of one of gold (Au), titanium (Ti), tantalum (Ta), molybdenum (Mo), ruthenium (Ru), platinum (Pt), tungsten (W), aluminum (Al), iridium (Ir), and nickel (Ni) or an alloy thereof. The piezoelectric layer 150 causes a piezoelectric effect whereby electrical energy is converted into mechanical energy in the form of an elastic wave and may selectively use zinc oxide (ZnO), aluminum nitride (AlN), doped aluminum nitride, lead zirconate titanate, quartz, and so on. The doped aluminum nitride may further include rare earth metal, transition metal, or alkaline earth metal. For example, the rare earth metal may include at least one of scandium (Sc), erbium (Er), yttrium (Y), and lanthanum (La) and the content of rare earth and content of the rare earth may be in the range of 1% to 20%. The transition metal may include at least one of hafnium (Hf), titanium (Ti), zirconium (Zr), tantalum (Ta), and niobium (Nb). The alkaline earth metal may include magnesium (Mg).

The membrane 130 may be formed on the sacrificial layer and may define a thickness of the air cavity 133 along with the support 134. The membrane 130 may also be formed of a material that is not easily removed during formation of the air cavity 133. For example, to form the air cavity 133, when halide-based etching gas, such as fluorine (F) and chlorine (Cl), is used to remove a portion of a sacrificial layer, the membrane 130 may be formed of a material with low reactivity with etching gas. The membrane 130 may include at least one of silicon dioxide ($SiO_2$) and silicon nitride ($Si_3N_4$). The membrane 130 may include a dielectric layer including at least one material of magnesium oxide (MgO), zirconium oxide ($ZrO_2$), aluminum nitride (AlN), lead zirconate titanate (PZT), gallium arsenide (GaAs), hafnium oxide ($HfO_2$), aluminum oxide ($Al_2O_3$), titanium oxide ($TiO_2$), and zinc oxide (ZnO) or may include a metal layer including at least one material of aluminum (Al), nickel (Ni), chromium (Cr), platinum (Pt), gallium (Ga), and hafnium (Hf).

A seed layer formed of aluminum nitride (AlN) may be formed on the membrane 130. The seed layer may be disposed between the membrane 130 and the first electrode 140. The seed layer may be formed of a dielectric or metal having a hexagonal close-packed (HCP) structure other than aluminum nitride (AlN). In the case of metal, for example, the seed layer may be formed of titanium (Ti).

The passivation layer 170 may be disposed on the second electrode 160 to prevent the second electrode 160 from being externally exposed. The passivation layer 170 may be formed of one insulating material of a silicon oxide-based material, a silicon nitride-based material, an aluminum nitride-based material, and an aluminum oxide-based material. The metal layer 180 may be formed on the externally exposed portions of the first electrode 140 and the second electrode 160.

The resonator 155 may be divided into an active region and a non-active region. The active region of the resonator 155 may be a region that vibrates and resonates in a certain direction according to a piezoelectric phenomenon generated in the piezoelectric layer 150 when electrical energy, such as a radio frequency signal, is applied to the first electrode 140 and the second electrode 160, and may correspond to a region at which the first electrode 140, the piezoelectric layer 150, and the second electrode 160 overlap each other in a vertical direction above the air cavity 133. The non-active region of the resonator 155 may be a region that does not resonate according to a piezoelectric phenomenon, even if electrical energy is applied to the first electrode 140 and the second electrode 160, and may correspond to a region outside the active region.

The resonator 155 may output a radio frequency signal with a specific frequency using a piezoelectric phenomenon. The resonator 155 may output a radio frequency signal with a resonant frequency corresponding to vibration according to a piezoelectric phenomenon of the piezoelectric layer 150.

Referring to FIG. 2, at least one via hole 113 penetrating through the substrate 110 in a thickness direction may be formed in a lower surface of the substrate 110 and a connection pattern 114 may be formed inside the via hole 113. In addition to penetrating the substrate 110, the via hole 113 may penetrate the insulating layer 115 and the auxiliary support 135 in the thickness direction.

The connection pattern 114 may be formed on an internal surface of the via hole 113, that is, an entire internal wall of the via hole 113. The connection pattern 114 may be manufactured by forming a conductive layer on the internal surface of the via hole 113. For example, the connection pattern 114 may be formed by depositing, coating, or filling at least one conductive metal of gold (Au), copper (Cu), and a titanium (Ti)-copper (Cu) alloy along with the internal wall of the via hole 113.

The connection pattern 114 may be connected to at least one of the first electrode 140 and the second electrode 160. For example, the connection pattern 114 may penetrate the substrate 110, the insulating layer 115, and the auxiliary support 135 to be electrically connected to at least one of the first electrode 140 and the second electrode 160. The connection pattern 114 formed on the internal surface of the via hole 113 may extend toward a lower surface of the substrate 110 and may be connected to a substrate connection pad disposed on the lower surface of the substrate 110. The connection pattern 114 may electrically connect the first electrode 140 and the second electrode 160 to the substrate connection pad.

The substrate connection pad may be electrically connected to an external substrate disposed below a fine dust concentration sensor through a bump. The bulk acoustic resonator 100 may perform a filtering operation of a radio frequency signal according to a signal applied to the first electrode 140 and the second electrode 160 through the substrate connection pad.

According to an example, the metal layer 180 or the like may be prevented from sagging downward through the connection pattern 114 that penetrates the auxiliary support 135, and is connected to the first electrode 140 and the second electrode 160 to support the first electrode 140 and the second electrode 160.

The cap 200 may be adhered to a stack structure forming the plurality of bulk acoustic resonators 100. The cap 200 may be formed in the form of a cover including an internal space for accommodating the plurality of bulk acoustic resonators 100 therein. The cap 200 may be formed like a hexahedron with an open lower surface and, accordingly, may include an upper portion and a plurality of lateral portions connected to the upper portion.

The cap 200 may have an accommodation portion formed at a central portion thereof to accommodate the resonator 155 of the plurality of bulk acoustic resonators 100. The stack structure may be adhered to a plurality of lateral portions at the adhesive region and the adhesive region of the stack structure may correspond to an edge of the stack structure. The cap 200 may be adhered to the substrate 110 and stacked on the substrate 110. The cap 200 may be adhered to at least one of the passivation layer 170, the membrane 130, the insulating layer 115, the first electrode 140, the piezoelectric layer 150, the second electrode 160, and the metal layer 180.

Figure 3:
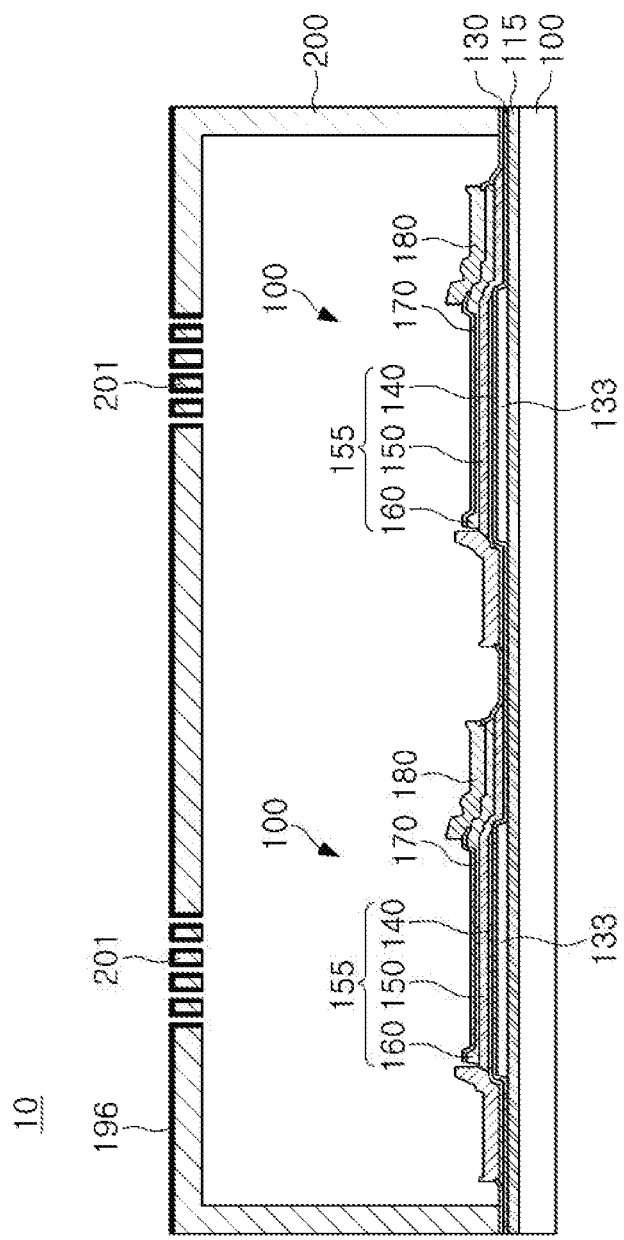
FIG. 3 is a cross-sectional view of a fine dust concentration sensor according to an example.

FIG. 3 is a cross-sectional view of a fine dust concentration sensor according to an example. The fine dust concentration sensor according to the example shown in FIG. 3 is similar to the fine dust concentration sensor according to the examples shown in FIGS. 1 and 2 and, in a description of the fine dust concentration sensor of FIG. 3, the same or repeated description of the fine dust concentration sensor of FIG. 1 is omitted and the bulk acoustic resonator of FIG. 3 is described in terms of a difference therefrom.

Referring to FIG. 3, the bulk acoustic resonator 100 may include the substrate 110, the insulating layer 115, the air cavity 133, and the resonator 155.

The substrate 110 may be formed of silicon (Si) and the insulating layer 115, for electrically separating the resonator 155 from the substrate 110, may be disposed on an upper surface of the substrate 110. The insulating layer 115 may be formed of one of silicon dioxide ($SiO_2$), silicon nitride (SiN), aluminum nitride (AlN), and aluminium oxide ($Al_2O_3$), and may be formed on the substrate 110 via chemical vapor deposition, RF magnetron sputtering, or evaporation.

The air cavity 133 may be disposed on the insulating layer 115. The air cavity 133 may be positioned below the resonator 155 in such a way that the resonator 155 vibrates in a certain direction. The air cavity 133 may be formed by forming a sacrificial layer on the insulating layer 115, forming the membrane 130 on the sacrificial layer, and then performing a process of etching and removing the sacrificial layer. The membrane 130 may function as an oxidation protective layer or may function as a passivation layer for protecting the substrate 110. The membrane 130 may include at least one of silicon dioxide ($SiO_2$), silicon nitride (SiN), aluminum nitride (AlN), and aluminium oxide ($Al_2O_3$).

An etch stop layer may be further formed between the insulating layer 115 and the air cavity 133. The etch stop layer may protect the substrate 110 and the insulating layer 115 from an etching process and may function as a base end required to deposit a plurality of different layers on the etch stop layer.

The resonator 155 may include the first electrode 140, the piezoelectric layer 150, and the second electrode 160. The first electrode 140, the piezoelectric layer 150, and the second electrode 160 may be sequentially stacked.

A common region at which the first electrode 140, the piezoelectric layer 150, and the second electrode 160 overlap each other in a vertical direction may be positioned above the air cavity 133.

The piezoelectric layer 150 causes a piezoelectric effect, whereby electrical energy is converted into mechanical energy in the form of an elastic wave and may selectively use zinc oxide (ZnO), aluminum nitride (AlN), doped aluminum nitride, lead zirconate titanate, and quartz. The doped aluminum nitride may further include rare earth metal, transition metal, or alkaline earth metal. For example, the rare earth metal may include at least one of scandium (Sc), erbium (Er), yttrium (Y), and lanthanum (La) and the content of rare earth and content of the rare earth may be in a range of 1% to 20%. The transition metal may include at least one of hafnium (Hf), titanium (Ti), zirconium (Zr), tantalum (Ta), and niobium (Nb). The alkaline earth metal may include magnesium (Mg).

A seed layer for enhancing crystal orientation of the piezoelectric layer 150 may be further disposed below the first electrode 140. The seed layer may be formed of one of aluminum nitride (AlN), doped aluminum nitride (doped AlN), zinc oxide (ZnO), and lead zirconate titanate (PPZT). The seed layer may include a dielectric or metal having a hexagonal close-packed (HCP) structure. The metal having the HCP structure may include titanium (Ti) and a Ti alloy.

The resonator 155 may be divided into an active region and a non-active region. The active region of the resonator 155 is a region that vibrates and resonates in a certain direction according to a piezoelectric phenomenon generated in the piezoelectric layer 150 when electrical energy, such as a radio frequency signal, is applied to the first electrode 140 and the second electrode 160, and may correspond to a region at which the first electrode 140, the piezoelectric layer 150, and the second electrode 160 overlap each other in a vertical direction above the air cavity 133. The non-active region of the resonator 155 may be a region that does not resonate according to a piezoelectric phenomenon, even if electrical energy is applied to the first electrode 140 and the second electrode 160, and may correspond to a region outside the active region.

The resonator 155 may output a radio frequency signal with a specific frequency using a piezoelectric phenomenon. The resonator 155 may output a radio frequency signal with a resonant frequency corresponding to vibration according to a piezoelectric phenomenon of the piezoelectric layer 150.

The passivation layer 170 may be disposed on the second electrode 160 of the resonator 155 to prevent the second electrode 160 from being externally exposed and being oxidized. The passivation layer 170 may be formed of one insulating material of a silicon oxide-based material, a silicon nitride-based material, an aluminum oxide-based material, and an aluminum nitride-based material. An electrode pad 180 for applying an electrical signal may be formed on the externally exposed portions of the first electrode 140 and the second electrode 160. The electrode pad 180 may include one of gold (Au), an Au alloy, copper (Cu), and a Cu alloy.

Figure 4A:
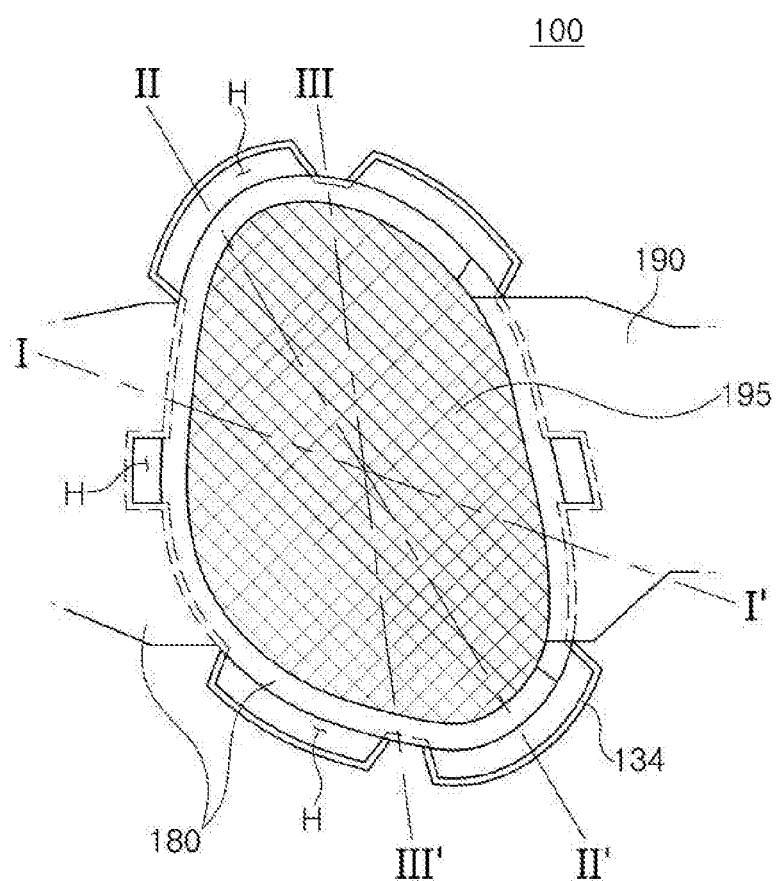
FIG. 4A is a plan view of an acoustic resonator according to an example.
Figure 4B:
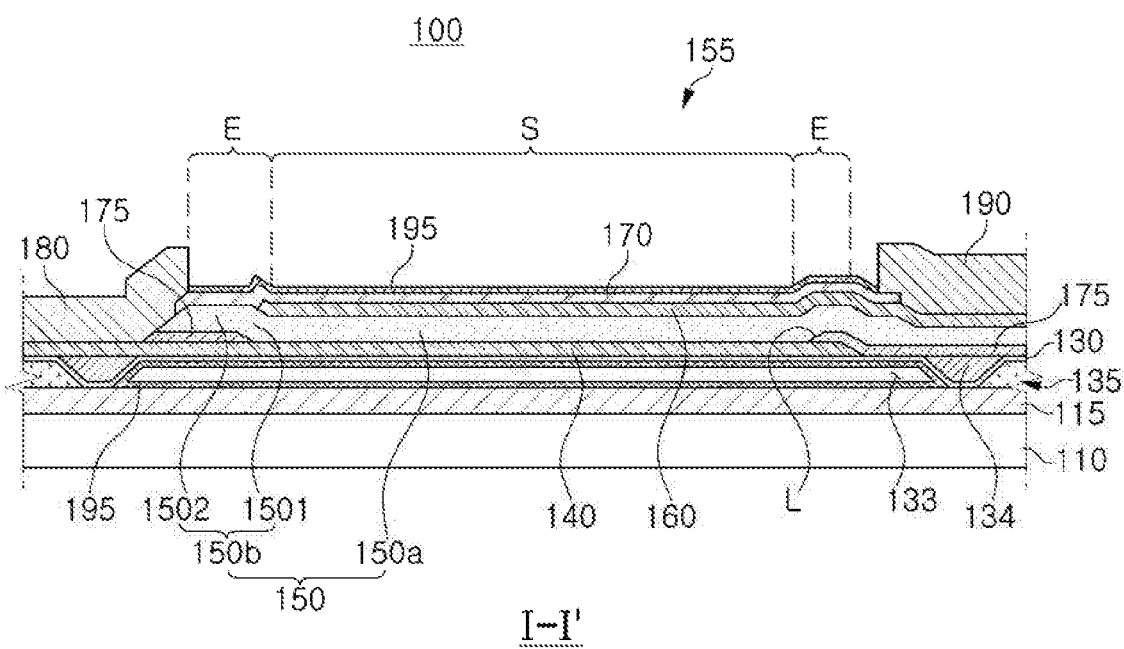
FIG. 4B is a cross-sectional view taken along a line I-I' of FIG. 4A.
Figure 4C:
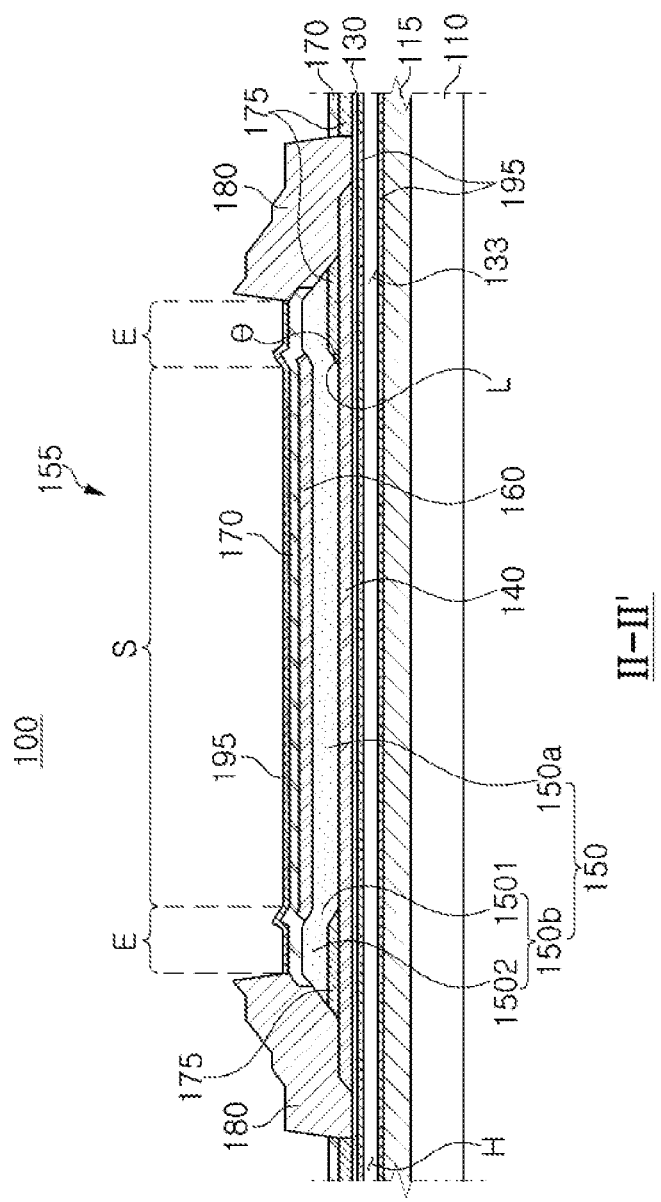
FIG. 4C is a cross-sectional view taken along a line II-II' of FIG. 4A.
Figure 4D:
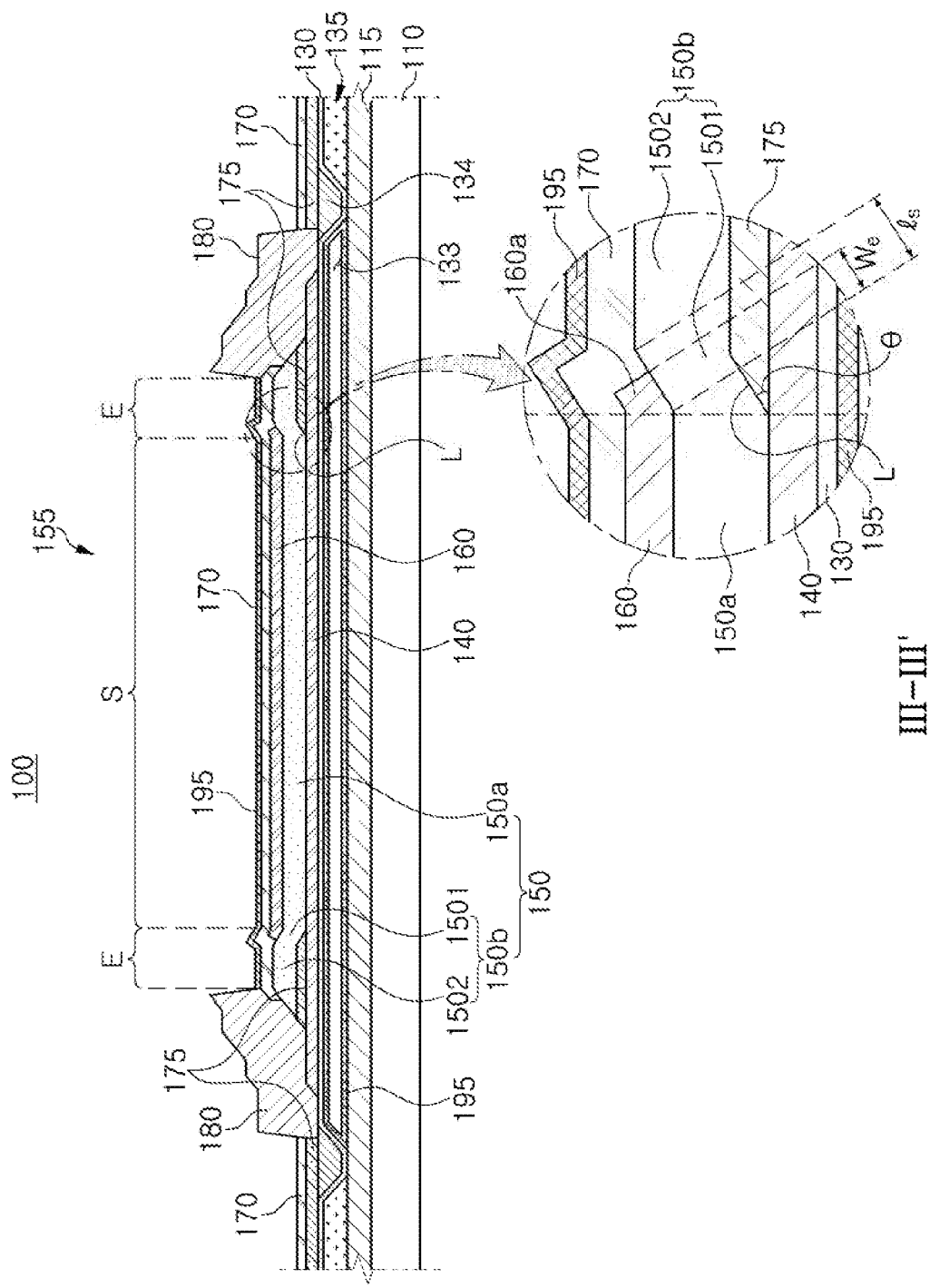
FIG. 4D is a cross-sectional view taken along a line III-III' of FIG. 4A.

FIG. 4A is a plan view of an acoustic resonator according to an example. FIG. 4B is a cross-sectional view taken along a line I-I' of FIG. 4A. FIG. 4C is a cross-sectional view taken along a line II-II' of FIG. 4A. FIG. 4D is a cross-sectional view taken along a line III-III' of FIG. 4A.

Referring to FIGS. 4A to 4D, the bulk acoustic resonator 100 according to an example may be a film bulk acoustic resonator (FBAR) and may include the substrate 110, the insulating layer 115, the membrane 130, the air cavity 133, the resonator 155, the passivation layer 170, and a hydrophobic layer 195.

The substrate 110 may be a silicon substrate. For example, a silicon wafer may be used as the substrate 110 or a silicon on insulator (SOI)-type substrate may be used as the substrate 110.

The insulating layer 115 may be disposed on an upper surface of the substrate 110 to electrically separate the substrate 110 and the resonator 155 from each other. The insulating layer 115 may prevent the substrate 110 from being etched by etching gas when the air cavity 133 is formed during a procedure of manufacturing the acoustic resonator.

The insulating layer 115 may be formed of at least one of silicon dioxide ($SiO_2$), silicon nitride ($Si_3N_4$), aluminium oxide ($Al_2O_2$), aluminum nitride (AlN), and aluminium oxide ($Al_2O_3$) and may be formed on the substrate 110 using any one process of chemical vapor deposition, RF magnetron sputtering, and evaporation.

The auxiliary support 135 may be formed on the insulating layer 115 and the air cavity 133, and the support 134 may be formed inside the auxiliary support 135. The air cavity 133 may be formed as an empty space and may be formed by removing a portion of the auxiliary support 135. As the air cavity 133 is formed in the auxiliary support 135, the resonator 155 formed on the auxiliary support 135 may be formed flat on the whole.

The support 134 may be disposed along a boundary of the air cavity 133. The support 134 may be included to prevent etching from proceeding over a cavity region during formation of the air cavity 133. A horizontal area of the air cavity 133 may be defined by the support 134 and a vertical area of the air cavity 133 may be defined by the thickness of the auxiliary support 135.

The membrane 130 may be formed on the auxiliary support 135 to define the thickness of the air cavity 133 along with the substrate 110. The membrane 130 may also be formed of a material that is not easily removed during formation of the air cavity 133.

For example, when halide-based etching gas, such as fluorine (F) or chlorine (CI), is used to remove a portion (e.g., a cavity region) of the auxiliary support 135, the membrane 130 may be formed of a material with low reactivity with the etching gas. The membrane 130 may include at least one of silicon dioxide ($SiO_2$) and silicon nitride ($Si_3N_4$).

The membrane 130 may include a dielectric layer including at least one material of manganese oxide (MgO), zirconium oxide ($ZrO_2$), aluminum nitride (AlN), lead zirconate titanate (PZT), gallium arsenide (GaAs), hafnium oxide ($HfO_2$), aluminum oxide ($Al_2O_3$), titanium oxide ($TiO_2$), and zinc oxide (ZnO), or may include a metal layer including at least one material of aluminum (Al), nickel (Ni), chromium (Cr), platinum (Pt), gallium (Ga), and hafnium (Hf). However, the disclosure is not limited to such materials.

A seed layer manufactured of aluminum nitride (AlN) may be formed on the membrane 130. A seed layer may be disposed between the membrane 130 and the first electrode 140. The seed layer may be formed of dielectric or metal having a HCP structure as well as AlN. In the case of the metal, for example, the seed layer may be formed of titanium (Ti).

The resonator 155 may include the first electrode 140, the piezoelectric layer 150, and the second electrode 160. In the resonator 155, the first electrode 140, the piezoelectric layer 150, and the second electrode 160 may be sequentially stacked from the bottom. In the resonator 155, the piezoelectric layer 150 may be disposed between the first electrode 140 and the second electrode 160.

The resonator 155 may be formed on the membrane 130 and, as a result, the resonator 155 may be formed by sequentially stacking the membrane 130, the first electrode 140, the piezoelectric layer 150, and the second electrode 160 on the substrate 110.

The resonator 155 may enable the piezoelectric layer 150 to resonate according to a signal applied to the first electrode 140 and the second electrode 160 to generate a resonant frequency and an antiresonant frequency.

When an insertion layer 175 is formed, the resonator 155 may be divided into a central portion S at which the first electrode 140, the piezoelectric layer 150, and the second electrode 160 are stacked approximately flat, and an expansion portion E at which the insertion layer 175 is interposed between the first electrode 140 and the piezoelectric layer 150.

The central portion S is a region disposed at the center of the resonator 155 and the expansion portion E is a region disposed along a peripheral of the central portion S. The expansion portion E refers to a region that extends outward from the central portion S.

The insertion layer 175 may include an inclination surface L with a thickness being increased away from the central portion S. In the expansion portion E, the piezoelectric layer 150 and the second electrode 160 may be disposed on the insertion layer 175. The piezoelectric layer 150 and the second electrode 160, which are positioned in the expansion portion E, may include an inclination surface along a shape of the insertion layer 175. The expansion portion E is defined to be included in the resonator 155 and, accordingly, resonance may also occur in the expansion portion E. However, the disclosure is not limited to such a configuration and, depending on a structure of the expansion portion E, resonance may occur only in the central portion S and not in the expansion portion E.

The first electrode 140 and the second electrode 160 may be formed of an electric conductor and, for example, may be formed of Au, Mo, Ru, Ir, Al, Pt, Ti, W, Pd, Ta, Cr, and Ni or metal including at least one thereof, but the disclosure is not limited to such materials.

The first electrode 140 may be formed with a larger area than the second electrode 160, and the first metal layer 180 may be disposed on the first electrode 140 along an external peripheral of the first electrode 140. The first metal layer 180 may be disposed to surround the second electrode 160.

The first electrode 140 may be disposed on the membrane 130 and, thus, may be formed flat on the whole. The second electrode 160 is disposed on the piezoelectric layer 150 and, thus, may be curved to correspond to a shape of the piezoelectric layer 150.

The second electrode 160 may be entirely disposed in the central portion S and may be partially disposed in the expansion portion E. The second electrode 160 may be divided into a portion disposed on a piezoelectric portion 150a of the piezoelectric layer 150 and a portion disposed on a bent portion 150b of the piezoelectric layer 150.

The second electrode 160 may be disposed to cover an entire portion of the piezoelectric portion 150a and a partial portion of an inclination portion 1501 of the piezoelectric layer 150. A second electrode 160a disposed in the expansion portion E may be formed with a smaller area than an inclination area of the inclination portion 1501 and the second electrode 160 in the resonator 155 may be formed with a smaller area than the piezoelectric layer 150.

The piezoelectric layer 150 may be formed on the first electrode 140. When the insertion layer 175 is formed, the piezoelectric layer 150 may be formed on the first electrode 140 and the insertion layer 175.

The piezoelectric layer 150 causes a piezoelectric effect whereby electrical energy is converted into mechanical energy in the form of an elastic wave and may selectively use zinc oxide (ZnO), aluminum nitride (AlN), doped aluminum nitride, lead zirconate titanate, and quartz. The doped aluminum nitride may further include rare earth metal, transition metal, or alkaline earth metal. For example, the rare earth metal may include at least one of scandium (Sc), erbium (Er), yttrium (Y), and lanthanum (La) and content of the rare earth may be in the range of 1% to 20%. The transition metal may include at least one of hafnium (Hf), titanium (Ti), zirconium (Zr), tantalum (Ta), and niobium (Nb). The alkaline earth metal may include magnesium (Mg).

The piezoelectric layer 150 may include the piezoelectric portion 150a disposed in the central portion S and the bent portion 150b disposed in the expansion portion E.

The piezoelectric portion 150a may be stacked directly on an upper surface of the first electrode 140. The piezoelectric portion 150a may be interposed between the first electrode 140 and the second electrode 160 to be formed flat along with the first electrode 140 and the second electrode 160. The bent portion 150b may extend outward from the piezoelectric portion 150a and may be defined as a region positioned in the expansion portion E. The bent portion 150b may be disposed on the insertion layer 175 and may be uplifted along a shape of the insertion layer 175. The piezoelectric layer 150 may be bent at a boundary between the piezoelectric portion 150a and the bent portion 150b, and the bent portion 150b may be uplifted to correspond to the thickness and shape of the insertion layer 175.

The bent portion 150b may include the inclination portion 1501 and an extension portion 1502. The inclination portion 1501 is a portion that is inclined along the inclination surface L of the insertion layer 175. The extension portion 1502 is a portion that extends outward from the inclination portion 1501.

The inclination portion 1501 may be formed in parallel to the inclination surface L of the insertion layer 175, and an inclination angle of the inclination portion 1501 may be the same as an inclination angle (θ of FIG. 4D) of the inclination surface L of the insertion layer 175.

The insertion layer 175 may be disposed along a surface formed by the membrane 130, the first electrode 140, and the support 134. The insertion layer 175 may be disposed around the central portion S to support the bent portion 150b of the piezoelectric layer 150. The bent portion 150b of the piezoelectric layer 150 may be divided into the inclination portion 1501 and the extension portion 1502 depending on a shape of the insertion layer 175.

The insertion layer 175 may be disposed in a region excluding the central portion S. For example, the insertion layer 175 may be disposed in an entire region except for the central portion S or may be disposed in a partial region. At least a portion of the insertion layer 175 may be disposed between the piezoelectric layer 150 and the first electrode 140. A lateral surface of the insertion layer 175 disposed along a boundary of the central portion S may have a thickness that increases in a direction away from the central portion S. The insertion layer 175 may have the inclination surface L that is formed with a lateral surface disposed adjacently to the central portion S and having a constant inclination angle θ.

When the inclination angle θ of the lateral surface of the insertion layer 175 is less than 5°, a thickness of the insertion layer 175 needs to be very thin or an area of the inclination surface needs to be excessively large to manufacture the insertion layer 175 and, thus, it may be difficult to embody the insertion layer 175.

When the inclination angle θ of the lateral surface of the insertion layer 175 is greater than 70°, an inclination angle of the inclination portion 1501 of the piezoelectric layer 150 stacked on the insertion layer 175 may also be greater than 90°. In this case, the piezoelectric layer 150 is excessively bent and, thus, the bent portion of the piezoelectric layer 150 may crack.

Accordingly, the inclination angle θ of the inclination surface L may be formed in the range between 5° and 70°.

The insertion layer 175 may be formed of a dielectric, such as silicon dioxide ($SiO_2$), aluminum nitride (AlN), aluminum oxide ($Al_2O_3$), silicon nitride (SiN), manganese oxide (MgO), zirconium oxide ($ZrO_2$), lead zirconate titanate (PZT), gallium arsenide (GaAs), hafnium oxide ($HfO_2$), aluminum oxide ($Al_2O_3$), titanium oxide ($TiO_2$), or zinc oxide (ZnO), but may be formed of a different material from the piezoelectric layer 150. It may be possible to form an empty space (an air cavity) as a region including the insertion layer 175. This may be embodied by forming an entire portion of the resonator 155, and then removing the insertion layer 175 during a manufacture process.

The thickness of the insertion layer 175 may be the same or similar to that of the first electrode 140. The thickness of the insertion layer 175 may be similar to a thickness of the piezoelectric layer 150 or may be smaller than a thickness of the piezoelectric layer 150. For example, the insertion layer 175 may be formed with a thickness equal to or greater than 100 Å and, in this case, may be formed with a smaller thickness than that of the piezoelectric layer 150. However, the disclosure is not limited to such a configuration.

The resonator 155 may be spaced apart from the substrate 110 through the air cavity 133 formed as an empty space.

The air cavity 133 may be formed by supplying etching gas (or etching solution) into an inlet hole (H of FIGS. 4A and 4C) and removing a portion of the auxiliary support 135 during a manufacture process of an acoustic resonator.

The passivation layer 170 may be disposed along a surface of the bulk acoustic resonator 100 to protect the bulk acoustic resonator 100 from the outside. The passivation layer 170 may be disposed along a surface formed by the second electrode 160, the bent portion 150b of the piezoelectric layer 150, and the insertion layer 175.

The passivation layer 170 may be formed of any one insulating material of a silicon oxide-based material, a silicon nitride-based material, an aluminum oxide-based material, and an aluminum nitride-based material but is not limited to such materials.

The first electrode 140 and the second electrode 160 may extend outward from the resonator 155 and the first metal layer 180, and a second metal layer 190 may be disposed on an upper surface of the extending portion.

The first metal layer 180 and the second metal layer 190 may be formed of a material such as gold (Au), a gold-tin (Au—Sn) alloy, copper (Cu), and a copper-tin (Cu—Sn) alloy.

The first metal layer 180 and the second metal layer 190 may function as a connection wiring for electrically connecting the first electrode 140 and the second electrode 160 of the acoustic resonator and an electrode of another acoustic resonator adjacently disposed thereto, or may function as an external connection terminal. However, the disclosure is not limited to such a configuration.

Although FIG. 4B illustrates a configuration in which the insertion layer 175 is disposed below the second metal layer 190, the disclosure is not limited to such a configuration and it may be possible to embody a structure from which the insertion layer 175 is removed, below the second metal layer 190.

The first metal layer 180 may penetrate the insertion layer 175 and the passivation layer 170 and may be adhered to the first electrode 140. As shown in FIG. 4C, the first electrode 140 may be formed with a larger area than the second electrode 160, and the first metal layer 180 may be formed in a peripheral portion of the first electrode 140.

The first metal layer 180 may be disposed along a periphery of the resonator 155 to surround the second electrode 160. However, the disclosure is not limited to such a configuration.

The second electrode 160 may be stacked on the piezoelectric portion 150a and the inclination portion 1501 of the piezoelectric layer 150. The second electrode 160a (refer to FIG. 4D) disposed on the inclination portion 1501 of the piezoelectric layer 150 of the second electrode 160, that is, the second electrode 160a disposed in the expansion portion E may be disposed only on a partial portion of an inclination surface of the inclination portion 1501, but not an entire portion thereof.

To enhance adhesive force between the hydrophobic layer 195 and the passivation layer 170, a precursor may be used. The precursor may be hydrocarbon having a silicon head or silioxane having a silicon head.

The hydrophobic layer 195 may also be disposed on an upper surface of the air cavity 133, as well as being disposed on the passivation layer 170. The hydrophobic layer 195 may be formed on at least one of a portion of lower and lateral surfaces of the air cavity 133, as well as the upper surface of the air cavity 133.

The resonator 155 is disposed on the air cavity 133 and, thus, an upper surface of the air cavity 133 may also affect a frequency change of the acoustic resonator. When the hydrophobic layer 195 is formed on an upper surface of the air cavity 133, a change in frequency of the acoustic resonator may be minimized.

Figure 5:
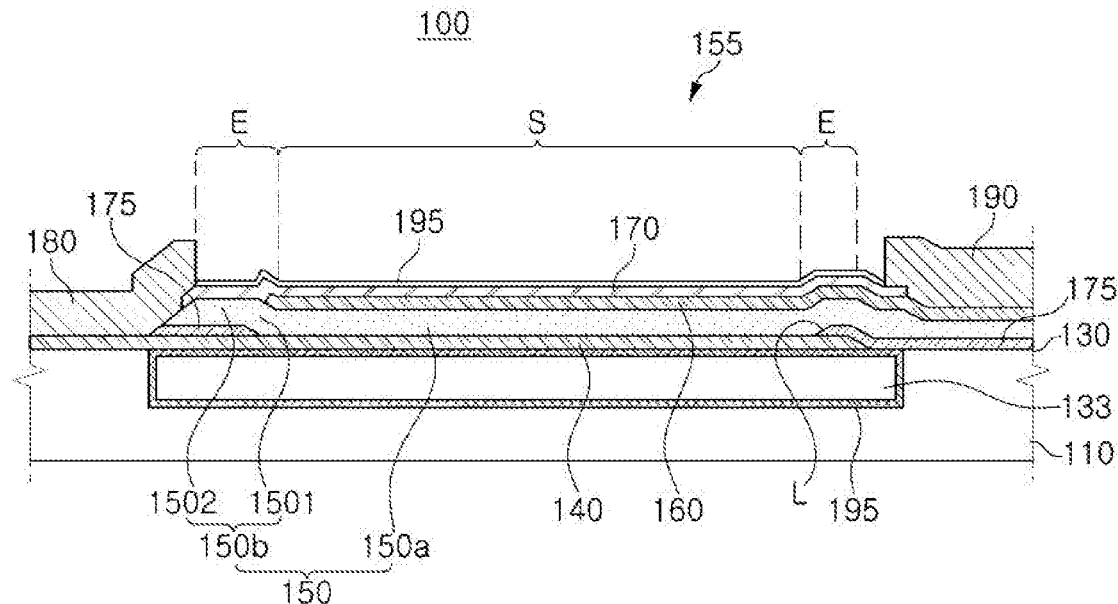
FIGS. 5 and 6 show a bulk acoustic resonator according to an example.
Figure 6:
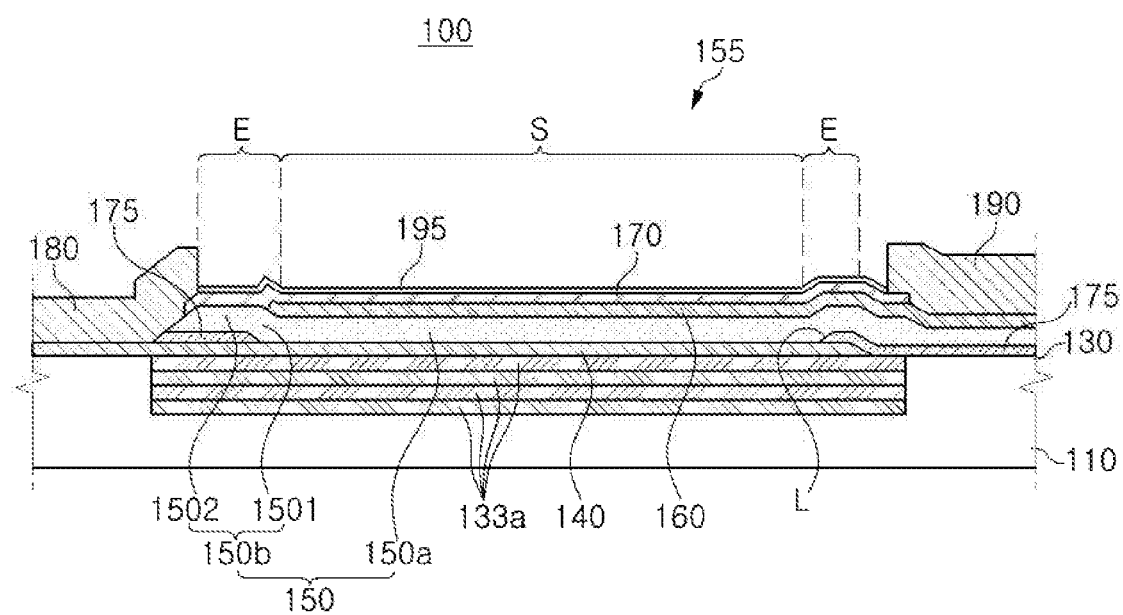

FIGS. 5 and 6 show a bulk acoustic resonator according to an example.

The bulk acoustic resonator 100 of FIGS. 5 and 6 is similar to the bulk acoustic resonator according to the example shown in FIG. 3A and, thus, a repeated description is omitted and the bulk acoustic resonator 100 of FIGS. 5 and 6 is described in terms of a difference therefrom.

Referring to FIG. 5, the air cavity 133 may be formed in the substrate 110 and the resonator 155 may be disposed on the substrate 110. Referring to FIG. 6, a plurality of reflective layers 133a may be disposed in a region in which the air cavity 133 of FIG. 5 is formed.

The reflective layers 133a may be formed of a silicon oxide-based material, a silicon nitride-based material, an aluminum oxide-based material, or an aluminum nitride-based material. The reflective layers 133a may be formed of a material including at least one or at least two of molybdenum (Mo), ruthenium (Ru), tungsten (W), and platinum (Pt). The reflective layers 133a may reflect a radio frequency signal output from the resonator 155.

Figure 7A:
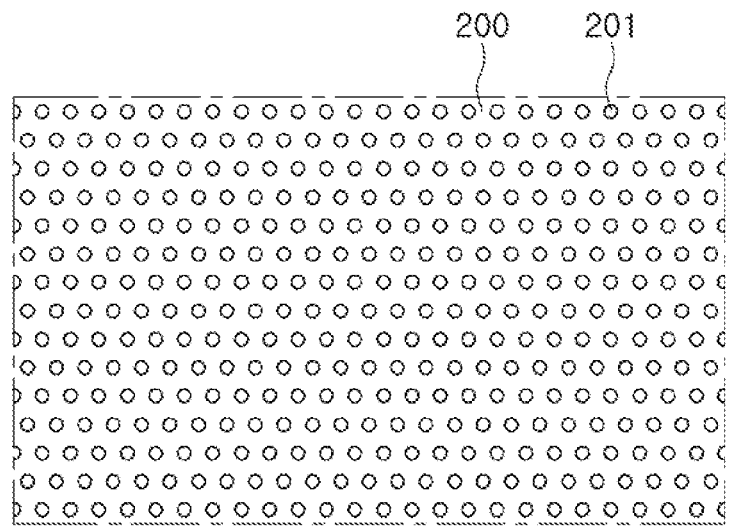
FIG. 7A is a partial top view of an upper portion of a cap according to an example.
Figure 7B:
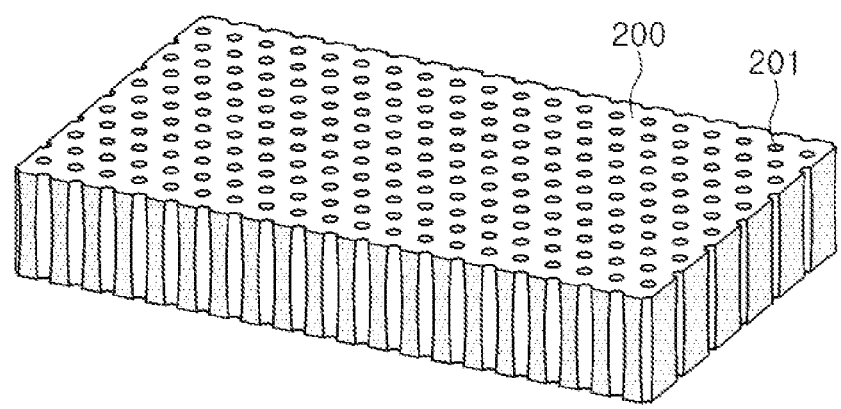
FIG. 7B is a partial perspective view of an upper portion of a cap according to an example.
Figure 8:
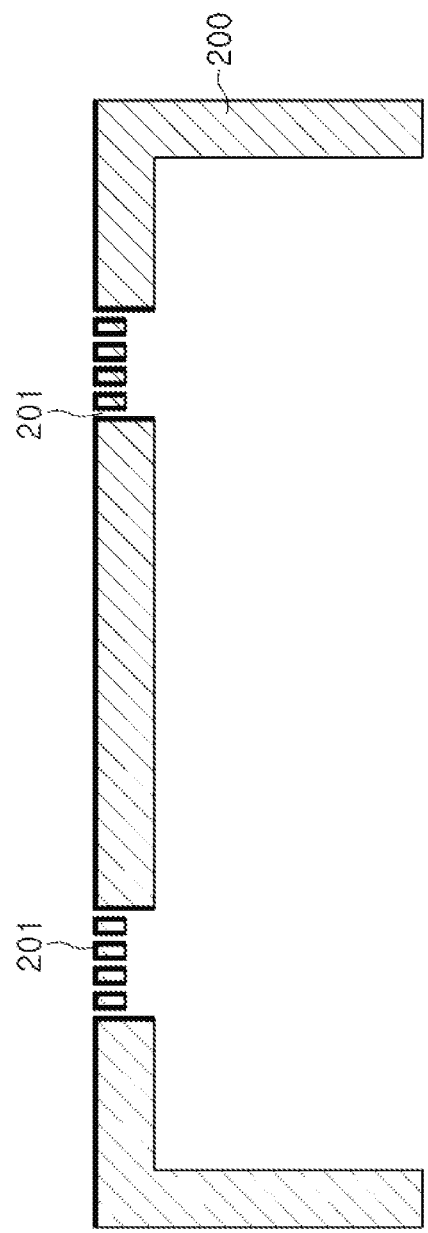
FIG. 8 shows a cap according to an example.

FIG. 7A is a partial top view of an upper portion of a cap according to an example. FIG. 7B is a partial perspective view of a cap according to an example. FIG. 8 shows a cap according to an example.

Referring to FIGS. 7A and 7B, a plurality of holes 201 may be formed in an upper portion of the cap 200. Fine dust outside the fine dust concentration sensor 10 may pass through the plurality of holes 201 formed in the cap 200. Referring to FIG. 8, the thickness of the cap 200 in a region in which the plurality of holes 201 is formed may be smaller than that of the cap 200 in a region in which the plurality of holes 201 is not formed.

The plurality of holes 201 may be formed with a polygonal shape such as a circular shape, an oval shape, a triangular shape, and a rectangular shape and may be formed with various shapes. An upper portion of the cap 200 may be formed by one of silicon (Si), silicon on insulator (SOI), glass, a dielectric, a polymer film, and a metal plate.

The upper portion of the cap 200 may be manufactured of silicon (Si) and silicon on insulator (SOI). A silicon (Si) substrate and silicon on insulator (SOI) substrate may be etched via a deep etching process to form a plurality of holes. The upper portion of the cap 200 may be manufactured of anodized aluminum oxide. The aluminum (Al) plate may be converted into anodized aluminum oxide by which a plurality of holes is formed by an anodizing process.

The plurality of holes 201 of the cap 200 may be formed to correspond to an active region of the bulk acoustic resonator. The plurality of holes 201 of the cap 200 may be formed on the active region of the bulk acoustic resonator. When fine dust introduced through the plurality of holes 201 of the cap 200 collects on the resonator 155, a frequency of a radio frequency signal output from the resonator 155 may be changed by mass of the fine dust. Accordingly, the fine dust concentration sensor 10 may measure concentration of the fine dust from the change in frequency.

Dust refers to a particle material that floats or flutters in the air and is generated when fossil fuel such as coal and petroleum is burn or is generated from discharge gas of a factory, a vehicle, and so on.

Dust is divided into total suspended particles (TSPs) with a particle size equal to or less than 50 µm and fine dust particulate matter (PM) with a very small particle size depending on a particle size. Fine dust may be re-divided into fine dust (PM10) with a diameter less than 10 µm and fine dust (PM2.5) with a diameter less than 2.5 µm. PM10 corresponds to about ⅕ to ⅐ of a diameter (50 to 70 µm) of a hair but PM2.5 is very fine and corresponds to only about 1/20 to 1/30 of a diameter of a hair. As such, it is not possible to recognize fine dust with the naked eye and, thus, fine dust stays in the air and penetrates the lung or the like through a respiratory organ or is moved into the body along a blood vessel to adversely affect health.

The World Health Organization (WHO) proposed a guideline for air quality with respect to fine dust (PM10 and PM2.5) in 1987 and the International Agency for Research on Cancer (IARC) under the World Health Organization (WHO) determined fine dust as first-group carcinogen (Group 1) which is verified as carcinogen of the human in 2013.

Each of the plurality of holes 201 of the cap 200 may have a size of 2 µm to 20 µm. When the size is less than 2 µm, it may not be easy to process a hole and, when the size is equal to or greater than 20 µm, it may be difficult to distinguish between sizes of fine dust such as fine dust PM10 and PM2.5. When the plurality of holes 201 is formed with a circular shape, the size refers to a diameter of a circular hole and, when the plurality of holes 201 is formed with a rectangular shape or a triangular shape, the size refers to a length of one side of a rectangular or triangular hole.

A size of each of the plurality of holes 201 may be 1 to 1/50 times the thickness of the upper portion of the cap 200. When the size of the hole 201 is greater than one time the thickness of the upper portion of the cap 200, as the upper portion of the cap is excessively thinned, the cap may crack. When the size of the hole 201 is smaller than 1/50 times the thickness of the upper portion of the cap 200, it may be difficult to process the hole in the thickness direction of the upper portion of the cap and it may also be difficult to uniformly embody the size of the hole. To detect fine dust for each size thereof, the size of the hole 201 of the cap 200 may be determined depending on a size of fine dust to be detected. When fine dust that passes through the hole 201 of the cap 200 for each size of fine dust reaches an active region of a resonator, as a resonant frequency or an antiresonant frequency of the resonator is changed, concentration of fine dust may be sensed for each size of fine dust.

According to an example, an upper surface of the upper portion of the cap 200 may be hydrophobic-coated with a hydrophobic material 196. For example, an internal surface of each of the plurality of holes 201 formed on the upper portion of the cap 200 may be coated with the hydrophobic material 196. The plurality of holes 201 of the cap 200 may be coated with the hydrophobic material 196 using a chemical vapor deposition (CVD) procedure and a physical vapor deposition (PVD) procedure. The hydrophobic material 196 may be formed using the aforementioned forming and deposition method.

The upper surface of the upper portion of the cap 200 or the internal surface of the hole 201 of the cap 200 may be coated with the hydrophobic material 196 to lower surface energy of the plurality of holes 201 and to prevent fine dust from being adsorbed to the plurality of holes 201. When fine dust to be detected is adsorbed to the hole 201 of the cap 200 to clog the hole 201 or other pollution materials clog the hole 201 of the cap 200, a problem in that sensing sensitivity of fine dust is remarkably degraded may be prevented.

The hydrophobic layer 195 may be formed on the passivation layer 170 disposed on the second electrode 160 of the resonator 155 and may also be formed inside the air cavity 133. According to an example, the hydrophobic material 196 may be formed on the upper surface of the upper portion of the cap 200 as well as the upper surface of the passivation layer 170 or the internal surface of the air cavity 133 to effectively prevent fine dust or pollution materials from being adsorbed and, accordingly, high-quality resonator performance may be achieved to enhance sensing sensitivity of fine dust.

When a bulk acoustic resonator is used in a humid environment or is kept at room temperature for a long time, a hydroxyl (OH) group is adsorbed onto a passivation layer of a bulk acoustic resonator and there is a problem in that a frequency is largely changed due to mass loading or performance of a bulk acoustic resonator is degraded.

Figure 9:
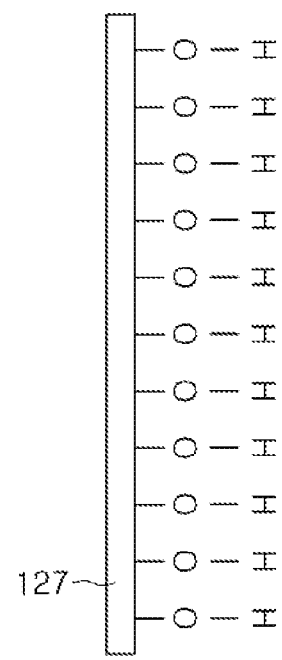
FIG. 9 illustrates a case in which a hydroxyl (OH) group is adsorbed onto a passivation layer on which a hydrophobic material is not formed.
Figure 10:
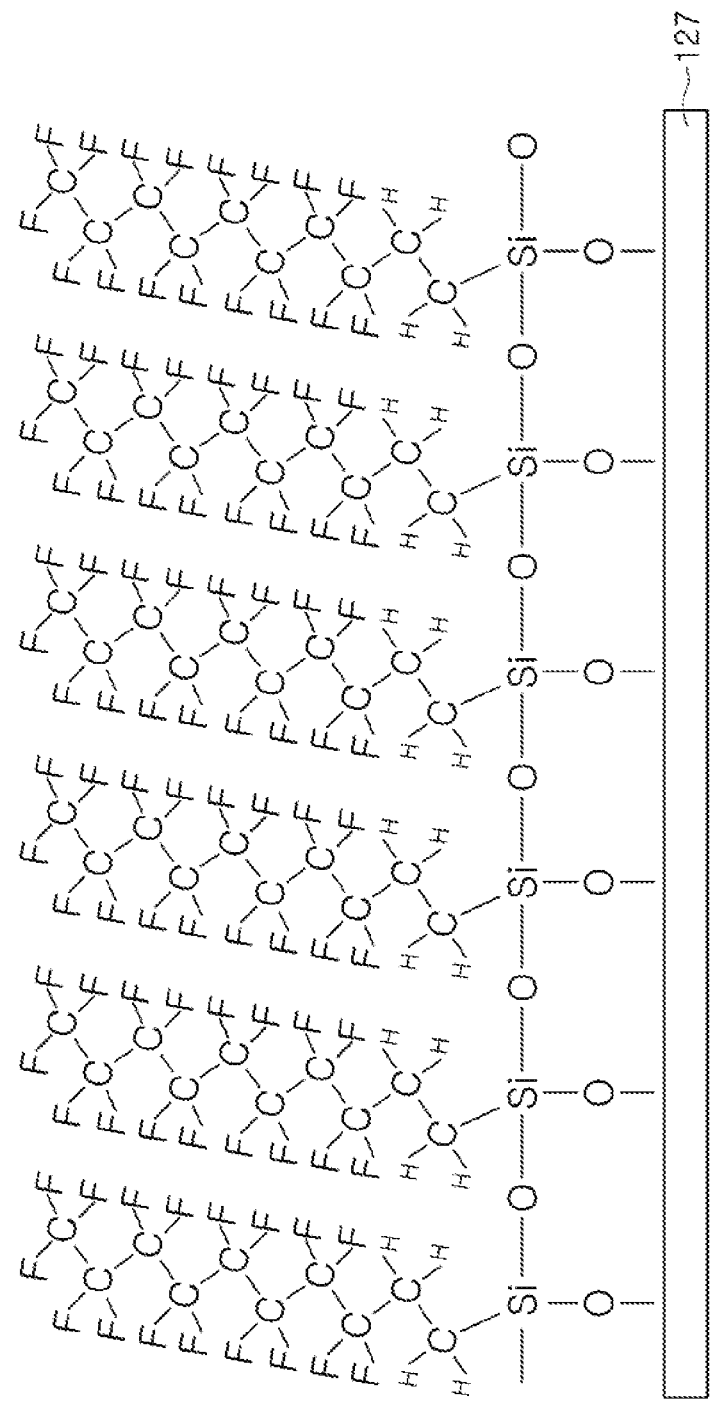
FIG. 10 illustrates a case in which a hydrophobic material is formed on a passivation layer.

FIG. 9 illustrates the case in which a hydroxyl (OH) group is adsorbed onto a passivation layer on which a hydrophobic material is not formed. FIG. 10 illustrates the case in which a hydrophobic material is formed on a passivation layer.

Referring to FIG. 9, when a hydrophobic material is not formed, if a bulk acoustic resonator is used in a humid environment or is kept at room temperature for a long time, a hydroxyl (OH) group may be adsorbed onto the passivation layer to form hydroxylate. Hydroxylate has high and unstable surface energy and, thus, water or the like is adsorbed onto hydroxylate to lower surface energy, thereby generating mass loading.

On the other hand, referring to FIG. 10, when a hydrophobic material is formed on the passivation layer, surface energy is low and stable and, thus, water, a hydroxyl (OH) group, or the like needs not to be adsorbed onto the passivation layer to lower surface energy. A hydrophobic material may prevent water, a hydroxyl (OH) group, or the like from being adsorbed to minimize a change in frequency and to uniformly maintain resonator performance. According to an example, the passivation layer 170 disposed on the second electrode 160 of the resonator 155 may be coated with a hydrophobic material to prevent fine dust from remaining on the resonator 155.

Figure 11:
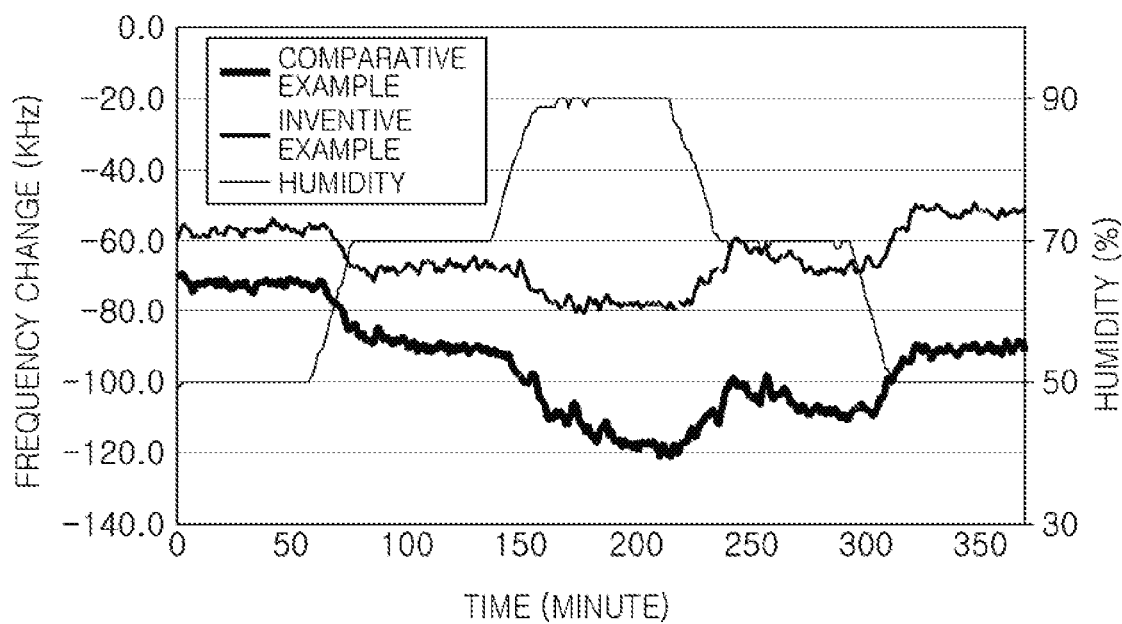
FIG. 11 is a graph showing a frequency change according to humidity and time with respect to an acoustic resonator in which a hydrophobic material is formed on a passivation layer and an acoustic resonator in which a hydrophobic material is not formed on a passivation layer.

FIG. 11 is a graph showing a frequency change according to humidity and time with respect to an acoustic resonator in which a hydrophobic material is formed on a passivation layer and an acoustic resonator in which a hydrophobic material is not formed on a passivation layer. According to an experiment method, the acoustic resonators according to the examples are put in a moisture absorption chamber and a change in frequency is measured as humidity is changed, as shown in FIG. 11.

As seen from FIG. 11, the acoustic resonator in which a hydrophobic material is formed on a passivation layer has a very low variation in frequency depending on a change in humidity and time. In addition, in the example in which a hydrophobic material is formed on a passivation layer, a variation in frequency when the experiment is terminated is smaller than a variation in frequency when the experiment is begun.

To enhance adhesive force between a hydrophobic material and a passivation layer, a precursor may be used.

Figure 12A:
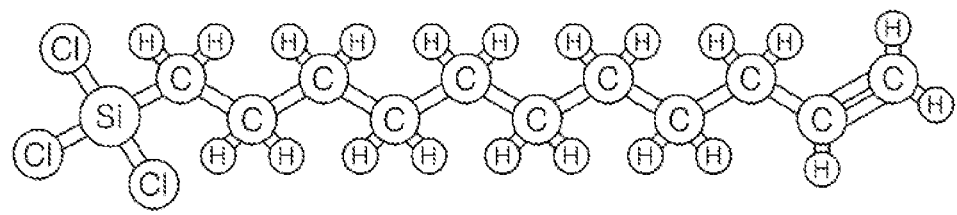
FIG. 12A and FIG. 12B are schematic diagrams of a molecular structure of a precursor used as an adhesion layer of a hydrophobic material.
Figure 12B:
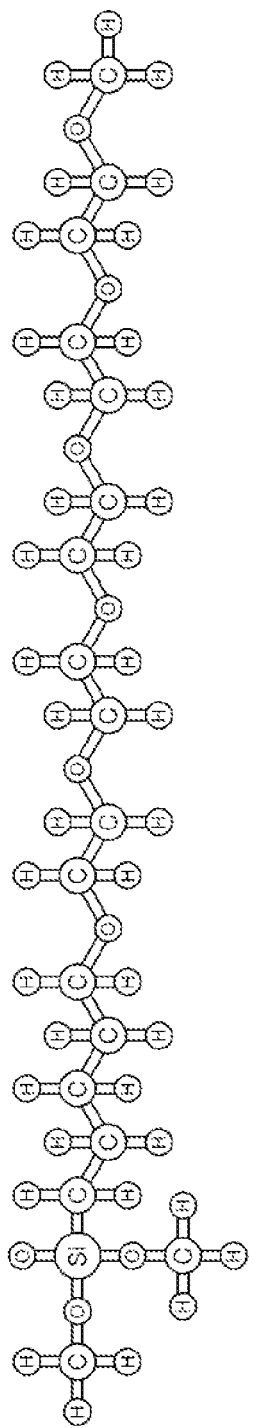

FIG. 12A and FIG. 12B are schematic diagrams of a molecular structure of a precursor used as an adhesion layer of a hydrophobic material. Referring to FIG. 12A and FIG. 12B, the precursor may be hydrocarbon having a silicon head or silioxane having a silicon head.

Figure 13:
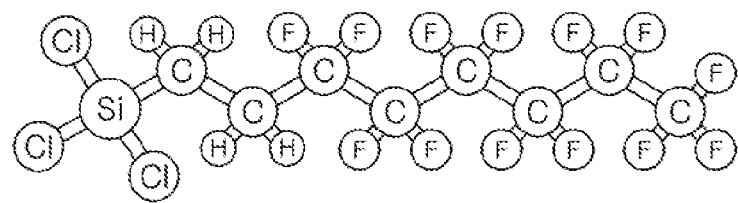
FIG. 13 is a schematic diagram of a molecular structure of a hydrophobic material.

FIG. 13 is a schematic diagram of a molecular structure of a hydrophobic material. Referring to FIG. 13, the hydrophobic material may be fluorocarbon but is not limited to such a material and, thus, the hydrophobic material may be a material that has a contact angle equal to or greater than 90° due to water after deposition. For example, the hydrophobic material may include a fluorine (F) component and may include fluorine (F) and silicon (Si).

The hydrophobic material may be used to form a mono layer but not a polymer or a self-assembled monolayer (SAM) and may have a thickness equal to or less than 100 A. When a hydrophobic material is formed of a polymer, a resonator is affected by mass due to the polymer. However, the acoustic resonator according to an example is formed as a mono layer and, thus, a change in frequency of the acoustic resonator may be minimized.

To detect fine dust for each size thereof, a size of a cap may be determined depending on a size of fine dust to be detected. When fine dust that passes through a hole of a cap for each size of fine dust reaches an active region of a resonator, as a resonant frequency or an antiresonant frequency of the resonator is changed, concentration of fine dust may be sensed for each size of fine dust.

When a hydrophobic material is formed on an upper surface of a cap or an internal surface of a hole of the cap and fine dust to be detected is adsorbed to the hole of the cap to clog the hole or other pollution materials clog the hole of the cap, a problem in that sensing sensitivity of fine dust is remarkably degraded may be overcome.

In addition, a hydrophobic material may be formed on an upper surface of an upper portion of a cap as well as the upper surface of the passivation layer or an internal surface of an air cavity to effectively prevent fine dust or pollution materials from being adsorbed and, thus, high-quality resonator performance may be embodied to enhance sensing sensitivity of fine dust.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A fine dust concentration sensor comprising:
   a bulk acoustic resonator; and
   a cap comprising an upper portion with holes, a lateral portion connected to the upper portion, and an internal space formed by the upper portion and the lateral portion accommodating the bulk acoustic resonator,
wherein an upper surface of the upper portion of the cap comprises a hydrophobic material.

2. The fine dust concentration sensor of claim 1, wherein an internal surface of each of the holes comprises the hydrophobic material.

3. The fine dust concentration sensor of claim 1, wherein the bulk acoustic resonator is configured to generate a resonant frequency or an antiresonant frequency used to measure a concentration of fine dust introduced through the holes.

4. The fine dust concentration sensor of claim 1, wherein the bulk acoustic resonator comprises a first electrode, a piezoelectric layer, and a second electrode, which are sequentially stacked.

5. The fine dust concentration sensor of claim 4, wherein the holes correspond to a region in which the first electrode, the piezoelectric layer, and the second electrode overlap each other in a stacking direction.

6. The fine dust concentration sensor of claim 4, wherein the bulk acoustic resonator comprises a passivation layer disposed on the second electrode and a hydrophobic layer disposed on the passivation layer.

7. The fine dust concentration sensor of claim 1, wherein the upper portion of the cap comprises one of silicon (Si), silicon on insulator (SOI), glass, a dielectric, a polymer film, and a metal plate.

8. The fine dust concentration sensor of claim 1, wherein each of the holes has a dimension in a range of 2 μm to 20 μm.

9. The fine dust concentration sensor of claim 1, wherein a dimension of each of the holes is 1 to 1/50 times a thickness of the upper portion of the cap.

10. A fine dust concentration sensor comprising:
a bulk acoustic resonator comprising a first electrode, a piezoelectric layer, and a second electrode, which are sequentially stacked in a stacking direction; and
a cap comprising an upper portion with holes and a lateral portion connected to the upper portion and accommodating the bulk acoustic resonator,
wherein the holes correspond to a region in which the first electrode, the piezoelectric layer, and the second electrode overlap each other in the stacking direction, and
wherein each of the holes has a dimension in a range of 2 μm to 20 μm.

11. The fine dust concentration sensor of claim 10, wherein an upper surface of the upper portion of the cap comprises a hydrophobic material.

12. The fine dust concentration sensor of claim 11, wherein an internal surface of each of the holes comprises the hydrophobic material.

13. The fine dust concentration sensor of claim 10, wherein the bulk acoustic resonator is configured to generate a resonant frequency or an antiresonant frequency used to measure a concentration of fine dust introduced through the holes.

14. The fine dust concentration sensor of claim 10, wherein the upper portion of the cap comprises one of silicon (Si), silicon on insulator (SOI), glass, a dielectric, a polymer film, and a metal plate.

15. The fine dust concentration sensor of claim 10, wherein a dimension of each of the holes is 1 to 1/50 times a thickness of the upper portion of the cap.

16. An apparatus comprising:
a cap defining an internal space and comprising holes in a surface thereof and a hydrophobic material covering at least a portion of the surface; and
a bulk acoustic resonator disposed in the internal space and configured to generate a resonant frequency or an antiresonant frequency used to measure a concentration of particle material introduced into the internal space through the holes.

17. The apparatus of claim 16, wherein the bulk acoustic resonator comprises a passivation layer and the hydrophobic material is disposed on the passivation layer.

18. The apparatus of claim 16, wherein the bulk acoustic resonator comprises a first electrode, a piezoelectric layer, and a second electrode stacked above an air cavity, and the hydrophobic material is disposed on internal surfaces defining the air cavity.

* * * * *